(12) United States Patent
Wang et al.

(10) Patent No.: US 9,499,501 B2
(45) Date of Patent: Nov. 22, 2016

(54) 2-MERCAPTOBENZOTHIAZOLE MANGANESE ZINC, PREPARATION METHOD THEREFOR AND APPLICATION THEREOF

(71) Applicant: Henan Xinxiang Academy of Agriculture Sciences, Henan (CN)

(72) Inventors: Zhenjun Wang, Henan (CN); Xu Zhang, Henan (CN); Limin Wang, Henan (CN); Hongyan Liu, Henan (CN); Senxiang Cheng, Henan (CN); Mengjiao Li, Henan (CN)

(73) Assignee: HENAN XINXIANG ACADEMY OF AGRICULTURE SCIENCES, Xinxiang, Henan (CN)

( * ) Notice: Subject to any disclaimer, the term of this patent is extended or adjusted under 35 U.S.C. 154(b) by 0 days.

(21) Appl. No.: 14/653,654

(22) PCT Filed: Nov. 30, 2013

(86) PCT No.: PCT/CN2013/088245
§ 371 (c)(1),
(2) Date: Jun. 18, 2015

(87) PCT Pub. No.: WO2014/094535
PCT Pub. Date: Jun. 26, 2014

(65) Prior Publication Data
US 2016/0000077 A1    Jan. 7, 2016

(30) Foreign Application Priority Data

Dec. 19, 2012 (CN) .......................... 2012 1 0553866

(51) Int. Cl.
| C07D 277/72 | (2006.01) |
| C07D 277/70 | (2006.01) |
| A01N 43/78 | (2006.01) |
| A01N 59/16 | (2006.01) |

(52) U.S. Cl.
CPC ............. *C07D 277/72* (2013.01); *A01N 43/78* (2013.01); *A01N 59/16* (2013.01); *C07D 277/70* (2013.01)

(58) Field of Classification Search
CPC .................................................... C07D 277/72
See application file for complete search history.

(56) References Cited

FOREIGN PATENT DOCUMENTS

| CN | 101514210 A | 8/2009 |
| CN | 102977052 A | 3/2013 |
| GB | 2 354 771 A | 4/2001 |

OTHER PUBLICATIONS

PCT International Search Report of the International Searching Authority dated Mar. 13, 2014 for International Application No. PCT/CN2013/088245 and English Translation, 6 pages.
F. M. Helaly et al., Controlling the Release of Active Iron and Manganese Ions from Styrene-Butadiene Rubber-Binding Matrix Containing Chloride Salts of Them, Journal of Applied Polymer Science, vol. 113, 811-817 (2009).

*Primary Examiner* — Matthew Coughlin
(74) *Attorney, Agent, or Firm* — Fitch, Even, Tabin & Flannery, LLP

(57) ABSTRACT

The present invention belongs to the technical field of agricultural fungicides and discloses a 2-mercaptobenzothiazole manganese zinc, preparation method therefor and application thereof. The chemical structure of the 2-mercaptobenzothiazole manganese zinc is shown as the above formula. Wherein m, n and n' are positive integers, $m=2(n+n')$, $n \geq n'$, $n:n'=1:1\sim9:1$. Materials are prepared according to the stoichiometric ratio of the target products; 2-mercaptobenzothiazole is dissolved in sodium hydroxide solution. The aqueous solution of water-soluble manganese salts and water-soluble zinc salts solution are successively added to 2-mercaptobenzothiazole sodium solution under stirring, followed by stirring for mixing well, then the solution being allowed to stand, filtered and washed with water to obtain filter cake, and then dried in vacuum to obtain 2-mercaptobenzothiazole manganese zinc. The present 2-mercaptobenzothiazole manganese zinc may be used as an agricultural fungicide. The present invention coordinates the surface of solid particles of 2-mercaptobenzothiazole manganese with zinc to form a stable clathrate of 2-mercaptobenzothiazole manganese and zinc. Tests show that the clathrate has excellent effect for controlling a plurality of diseases including apple *alternaria* leaf spot, pear scab, apple ring rot, apple anthracnose and the like.

2 Claims, 1 Drawing Sheet

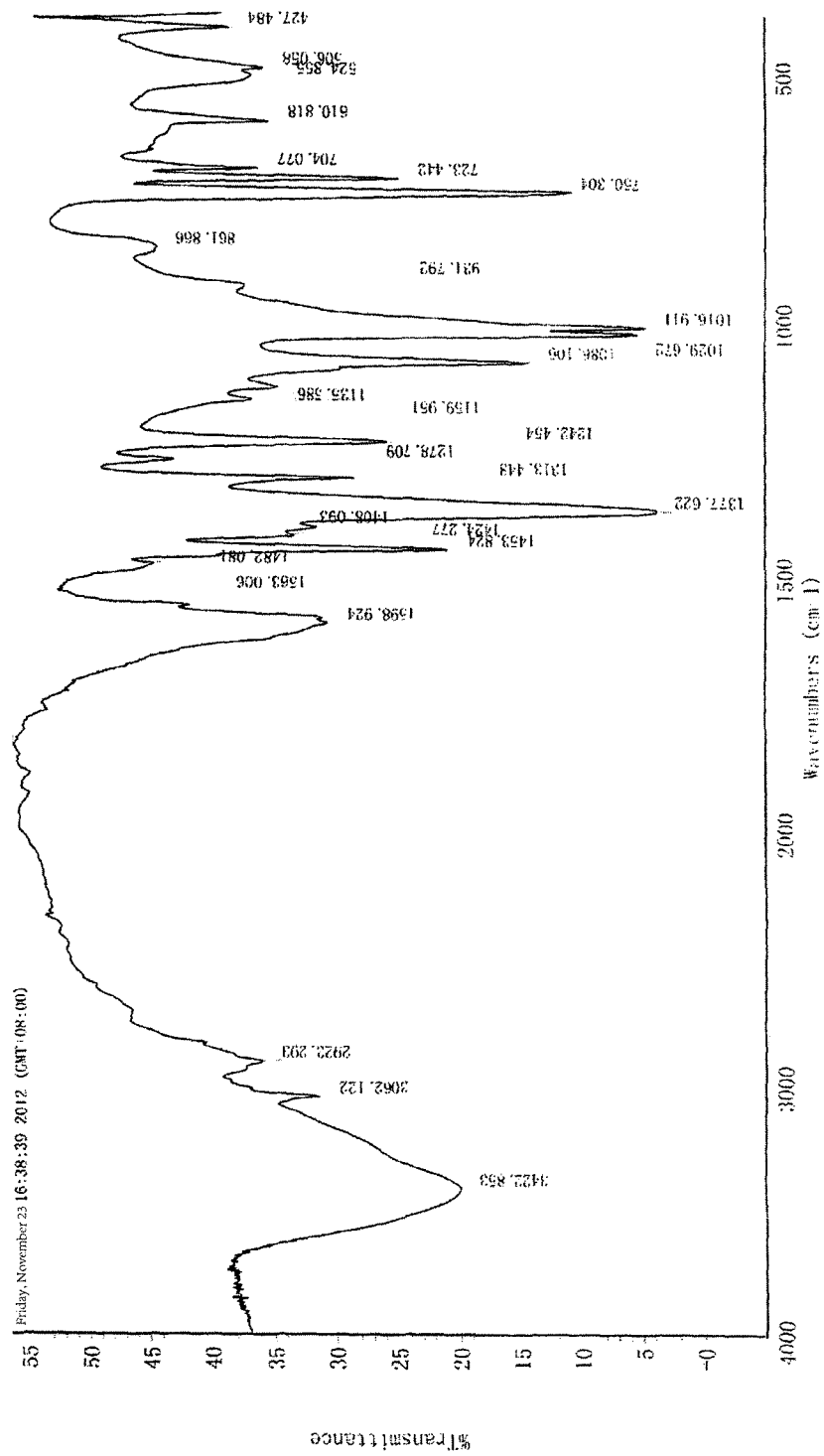

2-MERCAPTOBENZOTHIAZOLE MANGANESE ZINC, PREPARATION METHOD THEREFOR AND APPLICATION THEREOF

CROSS-REFERENCE TO RELATED APPLICATIONS

This application is a U.S. national phase application filed under 35 U.S.C. §371 of International Application PCT/CN2013/088245, filed Nov. 30, 2013, designating the United States, which claims priority from Chinese Application CN 201210553866.6, filed Dec. 19, 2012.

FIELD OF THE INVENTION

The present invention belongs to the technical field of agricultural fungicides, particularly, relates to a 2-mercaptobenzothiazole manganese zinc, preparation method therefor and application thereof.

DESCRIPTION OF THE PRIOR ART

Mancozeb is a broad-spectrum and protective organic sulfur fungicide, which is a coordination complex of maneb and zinc ion developed by Rohm and Haas Company in 1961. Mancozeb is of low toxicity and broad bactericidal spectrum, which can be used alone or in mixture with various systemic fungicides. It not only expands the existing bactericidal spectrum, but also improves the efficacy and delays the resistance by complementing the systemic fungicides. Mancozeb is an excellent protective agent and one of the important species of fungicides with wide current applications. However, there are some shortcomings with mancozeb. Studies showed that mancozeb metabolites contain ethylene thiourea (ETU). Ethylene thiourea is carcinogenic and affects thyroid function, which has potential threat on human health and the environmental safety. For food safety, it is a general tendency to ban the production and use of mancozeb. Use of mancozeb in early blooming and young fruit period is prone to cause phytotoxicity, which limits its use period. After years of continuous use in a large area, mancozeb's control effect has declined.

2-Mercaptobenzothiazole manganese has a good antibacterial effect. But since it is unstable in storage, and the release of manganese ions is too rapid in the application process which will result in damage to the blades of crops, it is difficult to be used as fungicides in practice.

SUMMARY OF THE INVENTION

The objects of the present invention are to provide a 2-mercaptobenzothiazole manganese zinc, preparation method therefor, and application thereof. The 2-mercaptobenzothiazole manganese zinc of the invention not only is stable in storage but also has good antibacterial effect and disease prevention effect.

To achieve the above objects, the present invention adopts technical solution as follows:

The chemical structure of 2-mercaptobenzothiazole manganese zinc is:

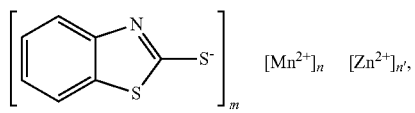

wherein m, n and n' are positive integers, and m=2(n+n'), n≥n', n:n'=1:1~9:1.

A preparation method comprises steps as follows:
(1) preparing the materials according to the stoichiometric ratio of the target products;
(2) dissolving 2-mercaptobenzothiazole in a sodium hydroxide solution;
(3) successively adding an aqueous solution of water-soluble manganese salt and an aqueous solution of a water-soluble zinc salt under stirring to the solution of 2-mercaptobenzothiazole sodium, followed by stirring for mixing well, then the solution being allowed to stand, filtered, washed with water and the filter cake being obtained, wherein the water-soluble manganese salt is one or more selected from the group of manganese sulfate, manganese chloride, manganese nitrate and manganese acetate, while the water-soluble zinc salt is one or more selected from the group of zinc sulfate, zinc chloride, zinc nitrate and zinc acetate;
(4) drying the filter cake in vacuum to obtain 2-mercaptobenzothiazole manganese zinc.

The 2-mercaptobenzothiazole manganese zinc of the present invention can be used as agricultural fungicide.

Further, the control object of the agricultural fungicide is apple *alternaria* leaf spot, pear scab, apple ring rot or apple anthracnose.

The agricultural fungicide is made into powder, wettable powder, granule or colloidal suspension agent.

Preferably, the 2-mercaptobenzothiazole manganese zinc is mixed with wetting and dispersing agent and filler before being ground and sieved and then a wettable powder is obtained, wherein the 2-mercaptobenzothiazole manganese zinc accounts for 30-90 wt %, the wetting and dispersing agent accounts for 0-20 wt % and the filler accounts for 0-65 wt %. The wetting and dispersing agent is one ore more selected from the group of calcium dodecylbenzenesulfonate, sodium dodecylbenzenesulfonate, sodium dodecylsulfonate, polyoxyethylene fatty acid ester, polyoxyethylene fatty acid alcohol, polyoxyethylene fatty acid amine, ethoxylated castor oil, sodium (potassium) lignin sulfonate, carboxymethyl alcohol, polyvinyl alcohol and polyvinyl ester. The filler is one or more selected from the group of diatomite, clay, gypsum, talc, kaolin and carbon-white.

Further, the 2-mercaptobenzothiazole manganese zinc of the present invention not only can be used alone, but also can be mixed with one or more fungicide (s) or pesticide(s) to formulate a binary or ternary mixture. In the mixture, 2-mercapto-benzothiazole manganese zinc accounts for 1-99 wt %. The fungicide is captan, folpet, zineb, mancozeb, thiram, captafol, iprodione, myclozolin, chlozolinate, hexaconazole, myclobutanil, tebuconazole, pencycuron, cymoxanil, iminoctadine acetate, prothiocarb, diethofencarb, cyclofuranid, esters iprodione, diniconazole, flutolanil, carbendazim, benomyl, triadimefon, cyproconazole, thiophanate-methyl, hymexazol, fenpropimorph, propamocarb, metalaxyl, benalaxyl, oxadixyl, methasulfocarb, pyrifenox, fenpropidin, TH-164, BAS480F, BAS490F, ICI5504, RH7592, MON24000, GCA219417, XRD-563, mepanipyrim, dimethomorph, fenpiclonil, fludioxanil, propiconazol, chlorothalonil, copper sulfate, dichlofluanid, fosetyl-Al or hymexazol. The pesticide is diazinon, bromopropylate, dicofol, 1605-methyl, 1605, fenitrothion, diazinon, chlorpyrifos, RH7988, RH5992, methomyl, monosultap, bisultap, cartap, carbaryl, permethrin, cypermethrin, tetramethrin, tefluthrin, cyfluthrin, fenvalerate, flufenoxuron, triflumuron, chlorfluazuron, fenpyroximate (NNI850), MK239, AC303630 (pyrroles compound), imidacloprid (NTN33893), ICIA5682, Fipronil, NI-25, CGA215944, TIA304, GR-572, CGA157419, CGA184699, PH-7023, XRD-473, fenoxycarb, fenazaquin, diafenthiuron, pyridaben (NC129), NC170, NC184, NC196, SU8801, clofentezine, avermectin or chlorantraniliprole toluamide.

The present invention coordinates the surface of solid particles of 2-mercaptobenzothiazole manganese with zinc to form a stable clathrate of 2-mercaptobenzothiazole manganese and zinc. Tests show that the clathrate has excellent effect for controlling a plurality of diseases comprising apple *alternaria* leaf spot, pear scab, apple ring rot, apple anthracnose and the like.

BRIEF DESCRIPTION OF THE DRAWINGS

FIG. 1 is an IR spectrum of the product of Example 1.

DETAILED DESCRIPTION OF THE PREFERRED EMBODIMENTS

Example 1

The preparation of 2-mercaptobenzothiazole manganese zinc:

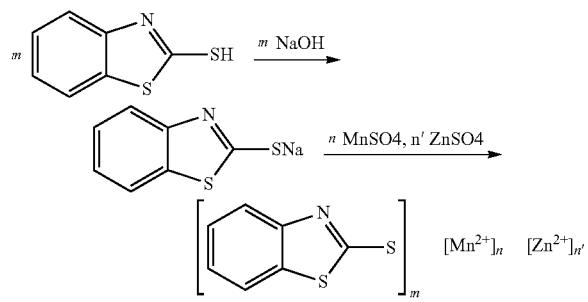

Sodium hydroxide 8.0 g (0.2 mol) was dissolved in 200 ml of distilled water. Under stirring, 2-mercaptobenzothiazole 33.4 g (0.2 mol) was added to the sodium hydroxide solution, followed by stirring to fully dissolve, and then a 2-mercaptobenzothiazole sodium solution was obtained.

An aqueous solution of manganese sulfate formulated with manganese sulfate 11.38 g (0.066 mol) and water 50 ml was added dropwise to the 2-mercaptobenzothiazole sodium solution in a period of 20~30 min, with temperature controlled at 20~30° C. and stirring for 0.5~1 h.

Zinc sulfate heptahydrate 9.88 g (0.034 mol) was dissolved in 50 ml of distilled water to obtain an aqueous solution of zinc sulfate. Under stirring, the aqueous solution of zinc sulfate was added dropwise to the above suspension of 2-mercaptobenzothiazole sodium—manganese sulphate. When the addition was completed, the temperature was controlled at 20~25° C. and the stirring was continued for 0.5~1 h. Then the mixture was allowed to stand for 1~2 h before being filtrated and washed with water 1~2 times, and thus a white precipitate was obtained. The white precipitate was then dried in vacuum, and 36.4 g of white solid, 2-mercaptobenzothiazole manganese zinc, was obtained.

Composition analysis: ICP, Mn, 10.05%; Zn, 6.11%; HPLC, 2-mercaptobenzothiazole, 82.4%, and the calculated value thereof was 83.8%. IR KBr cm$^{-1}$ (see FIG. 1): 3062, 2923, 1598, 1453, 1377, 1313, 1278, 1242, 1086, 1029, 1016, 750, 723, 704, 610.

After the 2-mercaptobenzothiazole manganese zinc underwent a mixture with wetting and dispersing agent, filler and others, a grind, and a sieving of 320-mesh, a wettable powder of 50 wt % of 2-mercaptobenzothiazole manganese zinc was obtained. The materials may take the following ratio: 2-mercaptobenzothiazole manganese zinc 50.0 wt %, calcium dodecylbenzenesulfonate 3.0 wt %, sodium lignin sulfonate 5.0 wt % and diatomite 42.0 wt %.

The prepared wettable powder of 50 wt % 2-mercaptobenzothiazole manganese zinc was tested in an antibacterial experiment, with blank (water) as blank control and a wettable powder of 50 wt % carbendazim as reference sample. And the strain for the test was *Alternaria mali* Roberts, provided by the Institute of Plant Protection of Henan Academy of Agricultural Science. The pathogenic bacteria was activated twice before the test (the germs stored at 4° C. were inoculated on a suitable culture medium to multiply and revert to the original pathogenicity). The culture medium was PDA medium (potato dextrose agar medium) consisting of: 200 g of peeled potato, 15 g of glucose, 10 g of agar powder and 1000 ml of distilled water, formulated in accordance with conventional methods. The inoculation test was conducted on a clean work bench and the culture dish was immediately put into the incubator after inoculation, and the temperature was 28° C. After 5 days, the investigation was performed when the control culture dish was covered with mycelia. Statistical results of bacteriostatic effect are shown in Table 1.

TABLE 1

| Bacteriostatic test of *Alternaria mali* Roberts | | | |
|---|---|---|---|
| Tested drugs | Concentration (ppm) (net)/ water diluted | Average daily extended length of mycelium (mm) | Inhibition rate (%) |
| 50 wt % wettable powder of the present invention | 67 | 1.53 | 64.82 |
| 50 wt % wettable powder of the present invention | 100 | 0.24 | 94.48 |
| 50 wt % wettable powder of the present invention | 200 | 0 | 100 |
| 50 wt % carbendazim | 500 | 2.97 | 31.72 |
| blank (water) | | 4.35 | |

Note:
The method for inoculation is cup and plate method with a diameter of 6 mm.

Example 2

Sodium hydroxide 4.0 g (0.1 mol) was dissolved in 200 ml of distilled water, 2-mercaptobenzothiazole 16.7 g (0.1 mol) was added to the sodium hydroxide solution under stirring, followed by stirring to fully dissolve, and then a 2-mercaptobenzothiazole sodium solution was obtained.

An aqueous solution of manganese nitrate formulated with 50% liquid manganese nitrate 8.95 g (0.025 mol) and water 50 ml was added dropwise to the 2-mercaptobenzothiazole sodium solution in a period of 20~30 min, with the temperature controlled at 20~30° C. and stirring for 0.5~1 h.

Zinc acetate dihydrate 5.54 g (0.025 mol) was dissolved in 50 ml of distilled water to obtain an aqueous solution of zinc acetate. Under stirring, the aqueous solution of zinc acetate was added dropwise to the above suspension of 2-mercaptobenzothiazole sodium—manganese nitrate. When the addition was completed, the temperature was controlled at 20~25° C. and stirring was continued for 0.5~1 h. Then the mixture was allowed to stand for 1~2 h before being filtrated and washed with water twice, and thus a white precipitate was obtained, which was then dried in vacuum. As a result, 18.3 g of white solid was obtained, which was identified as 2-mercaptobenzothiazole manganese zinc.

After the 2-mercaptobenzothiazole manganese zinc underwent a mixture with wetting and dispersing agent, filler and others, a grind, and a sieving of 320-mesh, a wettable powder of 90 wt % of 2-mercaptobenzothiazole manganese zinc was obtained. The materials may take the following ratio: 2-mercaptobenzothiazole manganese zinc 90.0 wt %, calcium dodecylbenzenesulfonate 6.0 wt %, carbon-white 3.0 wt % and sodium dodecylsulfonate 1.0 wt %.

Experimental field was set in the Bai Orchard, Guguzhai Town, Xinxiang County. The trees were 3 years old and the variety was Japanese Red Fuji Apple. Test group: 90 wt % wettable powder of 2-mercaptobenzothiazole manganese zinc 800 ppm; drug control groups: 50 wt % wettable powder of carbendazim 1000 ppm, 70 wt % wettable powder of Mancozeb 1400 ppm; and blank control group: CK (water). Each treatment was replicated four times. The drugs were sprayed before the apple *alternaria* leaf spot occurred. On sunny days, the selected times for spraying were before 10:00 and after 16:00. On cloudy days, the whole day was suitable for spraying. The drugs were sprayed once on April 28, once on May 7, once on May 17, once on August 28 and once on September 8, in 2012. The investigation adopted the method of four-way sampling from east, south, west and north, with 100 blades being investigated in each direction and four trees being investigated in each plot.

Investigation time: the morbidity degree of all the treatment groups were investigated when the blank control group reached the morbidity peak, and the control effects were calculated. The investigation date was September 29.

Grading criteria and calculation of control effects, the results are shown in Table 2.

Grade 0: no lesion;

Grade 1: lesion area accounted for less than 5% of the entire blade;

Grade 3: lesion area accounted for 6%-10% of the entire blade;

Grade 5: lesion area accounted for 11%-25% of the entire blade;

Grade 7: lesion area accounted for 26%-50% of the entire blade;

Grade 9: lesion area accounted for more than 50% of the entire blade;

$$\text{Disease index} = \frac{\sum\left(\begin{array}{c}\text{number of diseased blades in each grade} \times \\ \text{relative grade value}\end{array}\right)}{\text{total numbers of blades in the investigation} \times 9} \times 100$$

$$\text{Control effect} = \frac{\text{disease index of blank control district} - \text{disease index of treatment district}}{\text{disease index of blank control district}} \times 100$$

TABLE 2

The results of control effect on *alternaria* leaf spot in the field.

| Drugs | Concentration (ppm)/water diluted | Disease index before administration | Disease index | Control effect (%) |
|---|---|---|---|---|
| 90 wt % wettable powder of the present invention | 800 | 0 | 10.12 | 84.39 |
| 50 wt % carbendazim | 1000 | 0 | 39.26 | 39.45 |
| 70 wt % mancozeb | 1400 | 0 | 26.56 | 59.04 |
| CK | | | 64.84 | |

As can be seen from the experimental results, 800 ppm of 2-mercaptobenzothiazole manganese zinc of the present invention has a large scale field actual control effect of 84.39% for apple *alternaria* leaf spot, which is significantly higher than 39.45% of carbendazim and 59.04% of mancozeb, and the latter two are traditional fungicides.

Example 3

Sodium hydroxide 4.0 g (0.1 mol) was dissolved in 100 ml of distilled water. Under stirring, 2-mercaptobenzothiazole 16.7 g (0.1 mol) was added to the sodium hydroxide solution, followed by stirring to fully dissolve, and then a 2-mercaptobenzothiazole sodium solution was obtained.

An aqueous solution of manganese acetate formulated with manganese acetate tetrahydrate 11.14 g (0.045 mol) and water 50 ml was added dropwise to the 2-mercaptobenzothiazole sodium solution in a period of 20~30 min, with the temperature controlled at 20~30° C. and stirring for 0.5~1 h.

Zinc sulfate heptahydrate 1.45 g (0.005 mol) was dissolved in 50 ml of distilled water to obtain an aqueous solution of zinc sulfate. Under stirring, the aqueous solution of zinc sulfate was added dropwise to the above suspension of 2-mercaptobenzothiazole sodium—manganese sulphate. When the addition was completed, the temperature was controlled at 20~25° C. and stirring was continued for 0.5~1 h. Then the mixture was allowed to stand for 1~2 h before being filtrated and washed with water twice, and thus a white precipitate was obtained, which was then dried in vacuum. As a result, 17.8 g of white solid was obtained, which was identified as 2-mercaptobenzothiazole manganese zinc.

After the 2-mercaptobenzothiazole manganese zinc underwent a mixture with wetting and dispersing agent, filler and others, a grind, and a sieving of 320-mesh, a wettable powder of 30 wt % of 2-mercaptobenzothiazole manganese zinc was obtained. The materials may take the following ratio: 2-mercaptobenzothiazole manganese zinc 30.0 wt %, calcium dodecylbenzenesulfonate 4.0 wt %, carbon-white 3.0 wt %, sodium dodecylbenzenesulfonate 3.0 wt % and diatomite 60.0 wt %.

Test for control effect of pear scab was set in Wangfuzhuang Orchard, Langgongmiao Town, Xinxiang County, Henan Province. Test group: 30 wt % wettable powder of 2-mercaptobenzothiazole manganese zinc 800 ppm; drug control groups: 70 wt % Mancozeb 1400 ppm; blank control group: CK (water). Each treatment was replicated for four times. The drugs were sprayed before the pear scab occurred. On sunny days, the selected times for spraying were before 10:00 and after 16:00. On cloudy days, the whole day was suitable for spraying. The drugs were sprayed once on May 9, once on May 19 and once on June 10, in 2012. The investigation adopted the method of four-way sampling from east, south, west and north, with 100 blades being investigated in each direction and four trees being investigated in each plot. The calculation of disease index and control effect is the same as in Example 2.

TABLE 3

The results of control effect for pear scab of the drugs in the field.

| Drugs | Concentration (ppm)/water diluted | Disease index before administration | Disease index | Control effect (%) |
|---|---|---|---|---|
| 30 wt % wettable powder of the present invention | 800 | 0 | 12.06 | 82.32 |
| 70 wt % mancozeb CK | 1400 | 0 | 22.28 68.22 | 67.34 |

As can be seen from the experimental results, 800 ppm of 2-mercaptobenzothiazole manganese zinc has a significantly higher actual control effect than 1400 ppm of traditional fungicide mancozeb does.

Stability Control Test

The 2-mercaptobenzothiazole manganese zincs from Examples 1, 2 and 3 as well as the existing 2-mercaptobenzothiazole manganese were put in an open volumetric flask at room temperature respectively. The results showed that 2-mercaptobenzothiazole manganese turned dark brown in 60 days, while the color of 2-mercaptobenzothiazole manganese zinc did not change in 730 days. Thus the stability of 2-mercaptobenzothiazole manganese zinc was much higher than that of 2-mercaptobenzothiazole manganese salt.

The invention claimed is:

1. 2-mercaptobenzothiazole manganese zinc, characterized in that the chemical structure thereof is:

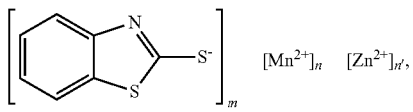

wherein m, n and n' are positive integers, and m=2(n+n'), n≥n', n:n'=1:1~9:1.

2. A method of preparing said 2-mercaptobenzothiazole manganese zinc according to claim 1, characterized in that the steps are as follows:
(1) preparing the materials according to the stoichiometric ratio of the target products;
(2) dissolving 2-mercaptobenzothiazole in sodium hydroxide solution;
(3) successively adding an aqueous solution of water-soluble manganese salt and an aqueous solution of a water-soluble zinc salt under stirring to the solution of 2-mercaptobenzothiazole sodium, followed by stirring for mixing well, then the solution being allowed to stand, filtered, washed with water and the filter cake being obtained, wherein the water-soluble manganese salt is one or more selected from the group of manganese sulfate, manganese chloride, manganese nitrate and manganese acetate, while the water-soluble zinc salt is one or more selected from the group of zinc sulfate, zinc chloride, zinc nitrate and zinc acetate;
(4) drying the filter cake in vacuum to obtain 2-mercaptobenzothiazole manganese zinc.

* * * * *